United States Patent [19]

Morrison et al.

[11] Patent Number: 5,551,424
[45] Date of Patent: Sep. 3, 1996

[54] FETAL PROBE APPARATUS

[75] Inventors: James P. Morrison, Batavia, Ill.; Samual K. Yue, Bloomington, Minn.

[73] Assignee: pHox Medical Optics, Inc., St. Charles, Ill.

[21] Appl. No.: 480,254

[22] Filed: Jun. 7, 1995

Related U.S. Application Data

[62] Division of Ser. No. 530,875, May 29, 1990.

[51] Int. Cl.$^6$ .............................. A61B 5/00; A61B 5/042
[52] U.S. Cl. ............................................ 128/634; 128/642
[58] Field of Search ...................................... 128/634, 635, 128/642, 633

[56] References Cited

U.S. PATENT DOCUMENTS

| | | | |
|---|---|---|---|
| Re. 28,990 | 10/1976 | Hon et al. | |
| 3,167,658 | 1/1965 | Richter | 250/239 |
| 3,224,433 | 12/1965 | Von Dalebor | 128/2 |
| 3,599,629 | 8/1971 | Gordy | 128/2.06 E |

(List continued on next page.)

FOREIGN PATENT DOCUMENTS

| | | |
|---|---|---|
| 671279 | 9/1958 | Canada. |
| 0072185A2 | 8/1981 | European Pat. Off.. |
| 0094749A3 | 4/1982 | European Pat. Off.. |
| 0104619A3 | 9/1982 | European Pat. Off.. |
| 0135840A2 | 8/1983 | European Pat. Off.. |
| 0135840 | 8/1984 | European Pat. Off.. |
| 0285307A1 | 3/1987 | European Pat. Off.. |
| 0454886A1 | 5/1990 | European Pat. Off.. |
| 1909882 | 2/1969 | Germany. |
| 2517129 | 4/1975 | Germany. |
| 2830412 | 7/1978 | Germany. |
| WO88/02616 | 10/1986 | WIPO. |
| WO90/04352 | 10/1988 | WIPO. |
| WO89/09016 | 10/1989 | WIPO. |
| 9001293 | 2/1990 | WIPO ................................ 128/642 |
| WO91/18549 | 5/1990 | WIPO. |

OTHER PUBLICATIONS

David A. Viniker, *The Fetal EEG (Detection of Oxygen Deprivation)*, British Journal of Hopsital Medicine, Nov. 1979.

*Silicon Diffused Pin Photodiodes SGD Series*, Electro–Optics.

*Planar Diffused Silicon Pin Photodiodes*, United Detector Technology.

*General Purpose Detectors*, Silicon Detector Corporation, Sep. 22, 1977.

C. Weller et al., *Fetal Electroencephalography Using a New, Flexible Electrode*, British Journal of Obstetrics and Gynoecology, Oct. 1981, vol. 88, pp. 983–986.

John W. Seeds et al., *The Relationship of Intracranial Infrared Light Absorbance to Fetal Oxygenation*, American Journal of Obstetrics and Gynoecology, Jul. 15, 1984, pp. 679–684.

Robert C. Goodlin et al., *Systolic Time Intervals in the Fetus and Neonate*, Obstetrics and Gynecology, vol. 39, No. 2, Feb. 1972, pp. 295–303.

Shah et al., *An Infra–Red Fibre Optic Device*, The Institute of Physics 1986, pp. 265–269.

(List continued on next page.)

Primary Examiner—Lee S. Cohen
Attorney, Agent, or Firm—Kinney & Lange, P.A.

[57] ABSTRACT

Disclosed is a fetal probe that is insertable through the mother's vagina and cervixes and connectable to a pulse oximeter for monitoring the EKG and oxygen saturation of hemoglobin of a fetus during labor and delivery. The probe incorporates at least one spiral electrode and optical fiber or fibers and/or solid state light sources for monitoring oxygen saturation. Light emitting diodes, or an optical fiber or fiber pair, transmit light of two different wavelengths through the fetal skin to perfused fetal tissue while either the EKG needle or another needle extends into fetal tissue and contains a light collecting optical fiber having a distal light collecting surface adjacent the relative needle distal end for collecting transmitted light that has passed through perfused fetal tissue that is interior of the fetal skin.

3 Claims, 5 Drawing Sheets

U.S. PATENT DOCUMENTS

| | | | |
|---|---|---|---|
| 3,602,213 | 8/1971 | Howell | 128/2.05 F |
| 3,647,299 | 3/1972 | Lavaliee | 356/41 |
| 3,659,586 | 5/1972 | Johns et al. | 128/2 E |
| 3,704,706 | 12/1972 | Herczfeld et al. | 128/2 R |
| 3,750,605 | 8/1973 | Ruttgers . | |
| 3,769,974 | 11/1973 | Smart et al. | 128/2.05 P |
| 3,804,080 | 4/1974 | Ruttgers et al. | 128/2.06 E |
| 3,814,081 | 6/1974 | Mori | 128/2 L |
| 3,822,695 | 7/1974 | Takayama . | |
| 3,841,314 | 10/1974 | Page | 128/2.05 P |
| 3,959,107 | 5/1976 | Horner et al. | 204/195 G |
| 3,973,555 | 8/1976 | Möller et al. . | |
| 3,983,866 | 10/1976 | Ulrich et al. | 128/2.05 P |
| 4,013,067 | 3/1977 | Kresse et al. | 128/2.05 R |
| 4,041,932 | 8/1977 | Fostick | 128/2 G |
| 4,091,803 | 5/1978 | Pinder | 128/2.05 P |
| 4,197,853 | 4/1980 | Parker | 128/635 |
| 4,200,110 | 4/1980 | Peterson et al. | 128/634 |
| 4,244,375 | 1/1981 | Farrar et al. | 128/642 |
| 4,281,645 | 8/1981 | Jöbsis . | |
| 4,281,659 | 8/1981 | Farrar et al. . | |
| 4,294,258 | 10/1981 | Bernard . | |
| 4,320,764 | 3/1982 | Hon | 128/635 |
| 4,321,931 | 3/1982 | Hon . | |
| 4,324,256 | 4/1982 | Vesterager | 128/635 |
| 4,350,165 | 9/1982 | Striese | 128/640 |
| 4,370,984 | 2/1983 | Cartmell | 128/640 |
| 4,396,017 | 8/1983 | Delpy et al. | 128/635 |
| 4,446,871 | 5/1984 | Imura | 128/633 |
| 4,519,396 | 5/1985 | Epstein et al. | 128/698 |
| 4,537,197 | 8/1985 | Hulka . | |
| 4,623,248 | 11/1986 | Sperinde | 356/41 |
| 4,644,956 | 2/1987 | Morgenstern | 128/642 |
| 4,651,741 | 3/1987 | Passafaro | 128/633 |
| 4,653,498 | 3/1987 | New, Jr. et al. | 128/633 |
| 4,658,825 | 4/1987 | Hochberg et al. | 128/642 |
| 4,685,464 | 8/1987 | Goldberger et al. | 128/633 |
| 4,718,417 | 1/1988 | Kittrell et al. | 128/303.1 |
| 4,773,422 | 9/1988 | Isaacson et al. . | |
| 4,776,340 | 10/1988 | Moran et al. | 128/634 |
| 4,781,195 | 11/1988 | Martin | 128/633 |
| 4,807,631 | 2/1989 | Hersh et al. | 128/633 |
| 4,815,805 | 3/1989 | Levinson et al. | 350/96.16 |
| 4,856,527 | 8/1989 | Karcher et al. | 128/634 |
| 4,893,625 | 1/1990 | Schuhmann | 128/635 |
| 4,903,701 | 2/1990 | Moore et al. | 128/419 PG |
| 4,907,876 | 3/1990 | Suzuki et al. | 356/41 |
| 4,913,151 | 4/1990 | Harui et al. | 128/634 |
| 4,925,299 | 5/1990 | Meisberger et al. | 356/40 |
| 4,934,371 | 6/1990 | Malis et al. | 128/642 |
| 4,938,218 | 7/1990 | Goodman et al. | 128/633 |
| 5,099,842 | 3/1992 | Mannheimer et al. | 128/633 |
| 5,109,849 | 5/1992 | Goodman et al. | 128/633 |
| 5,154,175 | 10/1992 | Gunther | 128/633 |
| 5,188,108 | 2/1993 | Secker | 128/633 |

OTHER PUBLICATIONS

Robert C. Goodlin M.D., *Intrapartum Fetal Heart Rate Responses and Plethysmographic Pulse,* American Journal of Obstetrics and Gynoecology, vol. 110, No. 2, May 15, 1971, pp. 210–226.

Goodlin, *Care of The Fetus,* Masson Publishing, New York, 1979, pp. 101–110.

John W. Seeds et al., *Near Infrared Spectrophotometry: A New Technique for Assessing Fetal Hypoxia,* Gynecology and Obstetrics, pp. 481–483.

*Noninvasive, Infrared Monitoring of Cerebral and Myocardial Oxygen Suffiency and Circulatory Parameters,* Science, Dec. 1977, pp. 1264–1267.

Robert C. Goodlin et al., *A New Fetal Scalp Electrode,* Obstetrics and Gynecology, vol. 35, No. 4, Apr. 1970, pp. 646–647.

N. S. Kapany, *Fiber Optics –Principles and Applications,* Academic Press, 1967, pp. 184–201.

Catharina M. Schram et al., *Pulse Oximetry In Fetal Lambs,* Dept. of Obstetrics & Gynecology.

Henk W. Jongsma et al., *Application of Transmission and Reflection Pulse Oximetry in Fetal Lambs,* Dept. of Obstetrics and Gynecology.

J. P. Payne et al., *Pulse Oximetry,* Springer–Verlag.

*American Journal Obstetrics/Gynecology* (Nov. 1985) "Fetal Subcutaneous Scalp $Po_2$ and Abnormal Heart Rate During Labor", pp. 565–566, J. G. Aarnoudse, et al.

*British Journal of Obstetrics & Gynecology* (1981) "Subcutaneous Oxygen Tension in the Fetal Scalp During Labor Continuous Monitoring With a Needle Electrode," 88:517, J. G. Aarnoudse.

FETAL PROBE APPARATUS

REFERENCE TO RELATED APPLICATION

This application is a divisional application of application Ser. No. 07/530,875, filed May 29, 1990.

FIELD OF THE INVENTION

The invention relates to apparatus for monitoring oxygen saturation of functional arterial hemoglobin and monitoring EKG of a fetus during labor and delivery.

BACKGROUND OF THE INVENTION

Monitoring of fetal heart rate trends through the use of an EKG electrode has long been used as an indicator of fetal well-being during labor and delivery. Increased awareness of serious adverse short and long term effects of fetal oxygen starvation (hypoxia) has resulted in a significant increase in the number of babies being monitored in this manner during birth.

Interpretation of heart rate trends in the fetal EKG record is subjective and a skill which requires substantial experience to acquire and maintain and has not been consistently reliable, especially in settings away from the high maternity rate urban areas.

In interpreting heart rate trends in the fetal EKG record, the physician attempts to infer the adequacy of oxygenation in the fetus. This technique is thus indirect and less than satisfactory since it is only after oxygen starvation has been occurring for some time that it is reflected in the EKG record. Also, the record itself is subject to non-deleterious phenomena such as uterine contractions. It is estimated that errors in interpretation of heart rate trends currently yields 50% false positives (conclusion that fetal distress is present when it is actually not) and 20% false negatives (instances where fetal distress is present but was not recognized).

There is an important difference in oximetry and pulse oximetry, oximetry referring to a general measurement of oxygenation of blood and tissue. In contrast pulse oximetry is an established method of determining in real time the relative oxygen saturation of arterial hemoglobin, and is used routinely in surgical suites and intensive care environments. Pulse oximetry provides an immediate and objective measure of oxygenation and requires little technical knowledge or interpretive expertise for its application.

In the opinion of some fetal physiology experts pulse oximetry is a superior technique for monitoring fetal status than pH since pulse oximetry provides real time monitoring of oxygen sufficiency and immediate corrective measures can be taken. If such insufficiency has persisted long enough for it to be reflected by a lower pH, it is likely that some neurological damage has already occurred.

U.S. Pat. No. 4,294,258 to Bernard discloses a measuring head for measuring an ionic or physico-chemical activity, notably pH in a part of, for example, the head of an unborn infant. The FIG. 15 embodiment includes a pair of hollow spiral claws. One of the claws contains a diaphragm sensitive to ionic activity while the second claw contains an extension of a KCL electrode.

Hochberg et al, U.S. Pat. No. 4,658,825, discloses a fetal probe having a single spiral needle containing a pair of optical fibers that are connected to a light source and light sensor exterior of the probe for monitoring EKG and a select chemical condition such as pH. Alternately a second spiral needle could be provided with one needle being used for pH and the other for EKG. The fiber pair carries light to and from the interior of the needle to detect color changes in a pH sensitive dye within the needle, it being stated that body fluids are allowed through a window in the needle and to an ion permeable dye containing membrane within the needle and adjacent to the needle distal end. There is no indication that the light is ever intended to leave through the window.

The Hochberg probe and other probes use pH as an indicator to imply an insufficient oxygen supply, this method being indirect. The logic used is that if the pH has decreased (become acidic), then the concentration of $CO_2$ has increased. If the concentration of the $CO_2$ is too high, then circulation/exchange at the placenta is compromised. If that is true, then oxygen supply is also likely insufficient.

Hon, U.S. Pat. Nos. 4,321,931 and Re. 28,990, disclose a conducting helix used as an electrode for use in monitoring fetal EKG.

U.S. Pat. No. 4,281,645 to Jobsis discloses a non-invasive structure and procedure for monitoring a state of metabolic activity in a body organ. That is, this patent is directed to the use of the optical characteristics of the enzyme cytochrome A to monitor cellular oxidative metabolism within an organ such as the heart, brain, or kidney by passing multiple wavelengths of visible and infrared light through the organ. The transmitters are being indicated as being on one side of the organ and the receivers on the opposite side of the organ, for example opposite sides of the head or chest.

Hulka, U.S. Pat. No. 4,537,197 discloses a fetal probe having a suction cup with a first aperture opening through its inner surface through which light from an optical fiber is transmitted to the fetal brain and an adjacent aperture through which the transmitted light is returned through an optical fiber. The light is to penetrate the skull to a depth where enzymatic activity associated with normal oxygenation in brain cells will be evident.

U.S. Pat. No. 3,973,555 to Moller discloses an electric cell assembly having an electrode that can be introduced and anchored in the living tissue of a fetus. The assembly is for measuring pH and includes a spiral to anchor the device.

Farrar et al, U.S. Pat. No. 4,281,659, discloses a probe for fetal monitoring. The disclosure is primarily directed to pH, however it is indicated that the arrangement is compatible with other measuring functions such as fetal ECG, $pO_2$ etc. The probe includes a base that threading mounts a probe and two spiral electrodes that serve to hold the base in place on the fetal skull.

Aaronoudse, J. G. "Subcutaneous Oxygen Tension Inthe Fetal Scalp During Labour Continuous Monitoring With A Needle Electrode", British Journal of Obstetrics and Gynaecology, 1981: 88: 517, discloses a pair of spirals for attaching the assembly to a fetal skull and a generally straight oxygen needle for measuring subcutaneous $Po_2$.

Takayama, U.S. Pat. No. 3,822,695, discloses a catheter system for simultaneously obtaining measurements of the blood pressure and the percentage content of oxygen contained in the blood within a blood vessel by inserting one end of an optical fiber bundle within a catheter into the blood vessel. Infrared rays and red light are passed through a catheter and there is individual detection of the amount of light reflected from the carboxyhemoglobin and oxyhemoglobin.

Isaacson, U.S. Pat. No. 4,773,422, discloses pulse oximeter apparatus for non-invasively measuring and indicating the percentage level of various constituents in arterial blood. Light of a plurality of separate wave lengths is sequentially passed through a portion of the body.

In order to overcome problems encountered with various types of prior art probes and to provide improved apparatus to simultaneously monitor fetal EKG and directly measure arterial hemoglobin oxygen saturation of a fetus during labor and delivery using the techniques of pulse oximetry, this invention has been made.

SUMMARY OF THE DISCLOSURE

The pulse oximetry fetal probe apparatus includes a probe body having a distal end, at least one needle spirally extending distally of the body, at least one of the needles being spiral and at least one optical fiber that extends within the distal end portion of the above needle or a second needle to receive light and carry the light signals back to a pulse oximeter external of the human body, and a light transmitter that is connected to the pulse oximeter and emits a light signal either adjacent to the external surface of the skin of a fetus or penetrates the skin of the fetus. A needle serves as an EKG electrode. The light transmitter may be a fiber or a pair of optical fibers that transmit two different wavelengths of light or a pair of light emitting diodes.

The probe includes optical fibers and/or solid state light sources (light emitting diodes) to permit the optical measurement of the oxygen saturation of fetal hemoglobin. The optical geometry of the probe is such that only optical signals which are derived from modulation by pulsatile variations in capillary blood volume of light which has been transmitted through perfused fetal tissue are analyzed and interference from light reflected from the surface of the fetal skin is excluded. In the event diodes are used, advantageously one emits a visible wavelength (red) and the other infrared.

Although it is satisfactory that the light transmitting distal surface be at the skin surface, it is preferred that the light collection distal surface be internally of the skin since light entering the monitor detector via a different path (i.e., not perfused tissue) can very easily seriously contaminate the measurement. A key consideration is that skin penetration ensures that the optical path be confined to perfused tissue.

One of the objects of this invention is to provide new and novel probe means for monitoring a chemical condition of the blood during labor and delivery. A further object of this invention is to provide new and novel means for determining a realtime relative oxygen saturation of arterial hemoglobin. Another object of this invention is to provide new and novel means usable with a conventional pulse oximeter monitor for transmitting a light signal to be scattered, reflected, absorbed and returned to the monitor light detector through a needle that penetrates the fetal skin. An additional object of the invention is to provide new and novel means to directly measure the oxygenation sufficiency of the arterial blood supply to ensure that an adequate supply of oxygen is being delivered.

DETAILED DESCRIPTION

Referring to FIGS. 1–4, the first embodiment of the probe of this invention, generally designate 10, includes a probe body 11, advantageously made of injection molded high density polystyrene or other biologically compatible material, that has a distal end surface 12. The major axial part of the body is cylindrical and has proximal flats 13 for facilitating the use of the probe.

A straight, hollow needle 15 extends axially beyond the distal end of the probe body and has a distal sharpened edge 15a distally inwardly of the body surface 12. An optical, light receiving fiber (light collector) 17 has its distal end radially adjacent the needle sharpened edge 15a and a proximal end connected to an adaptor 34 which incorporates an optical detector 18 whose output is electrically connected by a line 17a to the light (optical) signal input 18a of a conventional pulse oximeter monitor 19, for example one sold by Nonin Medical, Inc of Plymouth, Minn.

An EKG needle 22 has a proximal portion embedded in the probe body, the needle 22 including a spiral portion 22b that in part is embedded in the probe body while the remainder, including its distal sharpened end 22a, extending distally away from the body surface 12. The needle may be solid or tubular. The needle spiral portion exterior of the probe body extends through about ¾ to 1½ turns. A lead 23 electrically connects the EKG needle to the adaptor 34 and thence through line 23a to the EKG terminal of the EKG monitor 31. The central axis of the spiral portion 22b and the central axis of the straight needle that are in radial adjacent relationship to one another are coextensive.

A first and a second light emitting diodes (light transmitters) 25, 27 respectively are at least partially embedded in the distal end portion of the probe body on diametrically (transverse) opposite sides of the straight needle 15 and in radial spaced relationship to the straight needle 15, but adjacent thereto. The light emitting portions (light transmittal distal surfaces) of the diodes either extend slightly distally away from the surface 12 or are located proximally closely adjacent to the surface 12 and the light is emitted through apertures in the probe body. Diode 25 emits visible red (for example about 660 nm) while diode 27 emits infrared (for example about 920 nm). Conduits 28 and 29 are respectively connected to diodes 25 and 27 and the adaptor and thence through lines 28a and 29a to the source portion 30 of the monitor. The light emitting diodes are connected in parallel, but with opposite polarity (cathode-anode and anode-cathode) so that the wire pair 28, 29 can drive them alternately using pulses of opposite polarity.

Advantageously the leads 23, 28, 29 from within the probe body adjacent to the proximal end of the probe body to the adaptor 34 may be coiled in a triple filar manner about the radial adjacent parts of the optical fiber 17. Preferably the straight needle terminates axial intermediate the distal and proximal ends of the probe body. Advantageously, the distal terminal end of the fiber insulation 17b (thickness of insulation relative to rest of fiber being exaggerated) of the fiber 17 terminates adjacent to the proximal end of the needle 15 while the non-insulated portion extends within the needle 15 as indicated above. The probe is a disposable item. If the monitor is of a type that includes the facility to monitor EKG, then a separate EKG monitor 31 would not be required.

In use, the probe is rotated to attach the probe head to the fetal scalp with at least the diodes abutting against the fetal head skin surface if they extend distally of the surface 12, otherwise the surface 12 abuts against the skin, and the light is emitted at the skin surface to penetrate the skin and the perfused tissue below the skin where the light is scattered, reflected, and absorbed and modulated by the pulsatile varying capillary blood volume.

At this time the straight needle 15 penetrates the fetal tissue a few millimeters below the skin. The fiber in the needle 15 serves to collect the modulated light and a light (optical) signal is returned to the light signal input portion 18a of the monitor 19 that is external of the mother and the probe body. The proximity of the diodes relative to the straight needle ensures that the infrared and visible optical paths are similar. The light in traveling from the diodes passes through the skin and adjacent tissues to the distal tip of the fiber 17 in needle 15 where the light is collected and returned to the detector 18. Both the visible and the infrared signals experience similar optical modulations with one exception. The visible signal experiences an additional absorption which is principally a function of the relative oxygen saturation of the arterial hemoglobin in the optical path.

Both the visible and infrared signals from the detector vary as a function of probe placement, skin pigmentation, fetal motion, and other factors in an unpredictable manner. However, both signals experience similar variations with the exception of the visible absorption due to varying oxygen saturation. Thus, by using the infrared signal as a reference, monitoring the visible signal permits the determination of arterial oxygen saturation for the fetus. Additionally, since both signals vary with each fetal heart beat, the fetal heart rate is directly obtained. This permits direct comparison with the heart rate as monitored with standard fetal EKG methods.

Even though the needle 15 has been described and shown as having its proximal end terminating within the probe body, it is to be understood that needle 15 may have its proximal end terminating proximally outwardly of the probe body.

Figure 1:
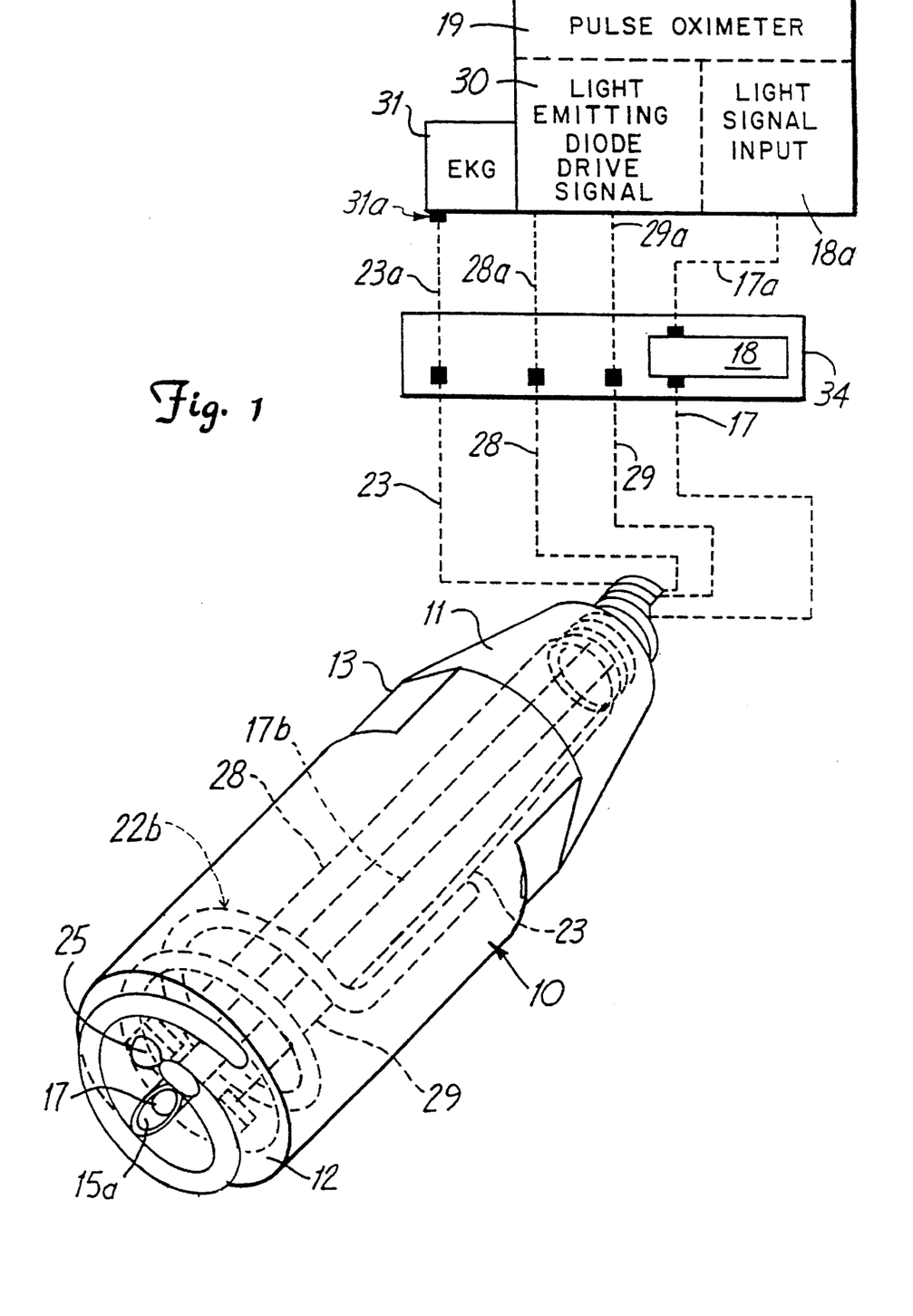
FIG. 1 is a perspective view of the first embodiment of the probe of this invention.
Figure 2:
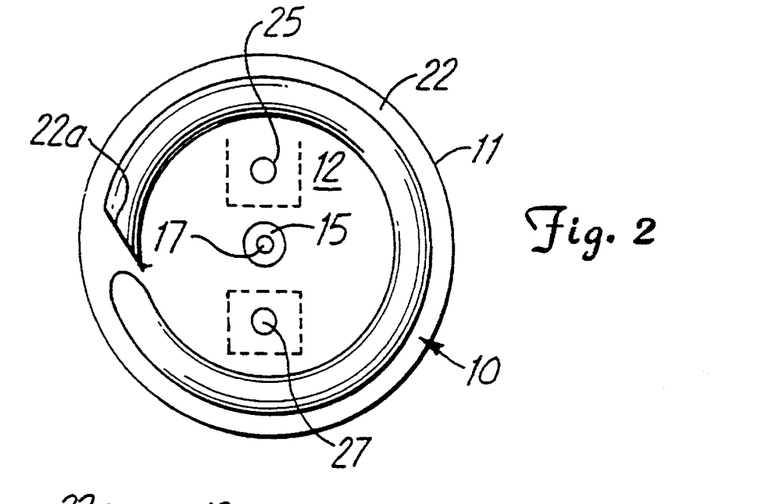
FIG. 2 is a distal end view of the first embodiment of the probe.
Figure 3:
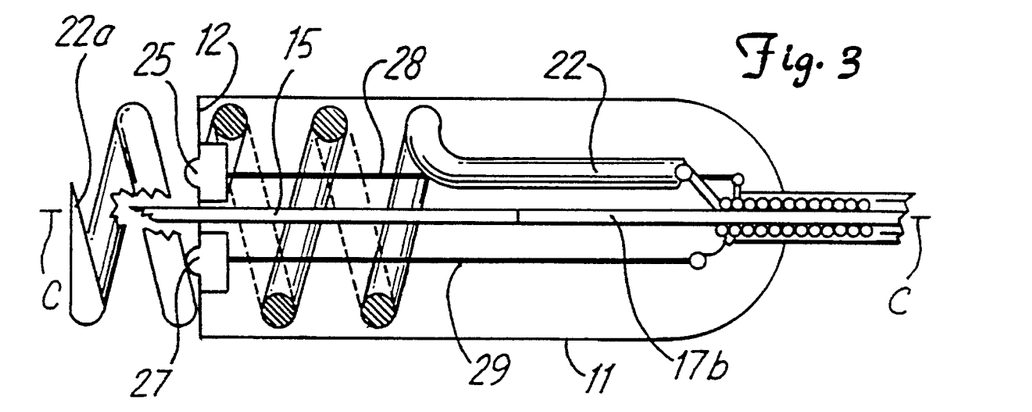
FIG. 3 is a somewhat diagramatic section view of the first embodiment.
Figure 4:
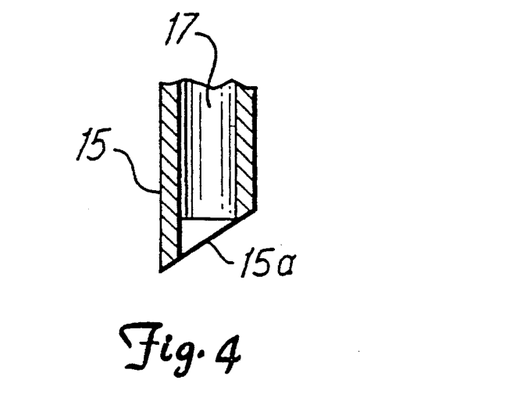
FIG. 4 is a fragmentary cross sectional view of the straight needle of the first embodiment.
Figure 5:
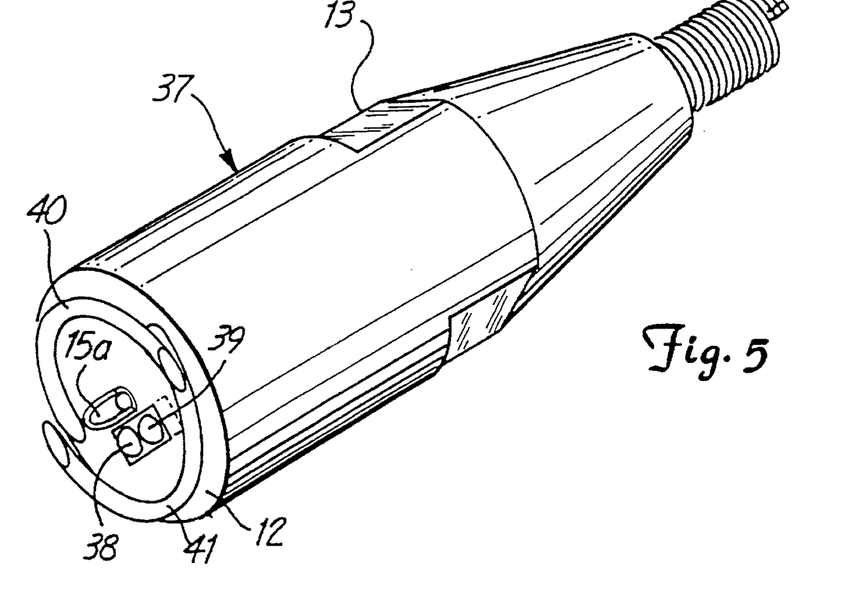
FIG. 5 is a perspective view of the second embodiment of the invention.
Figure 6:
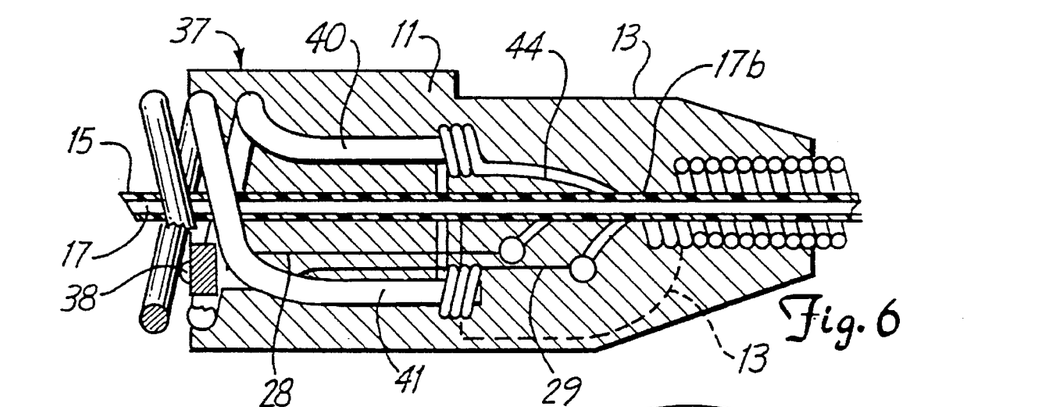
FIG. 6 is for the most part a cross sectional view of the second embodiment.
Figure 7:
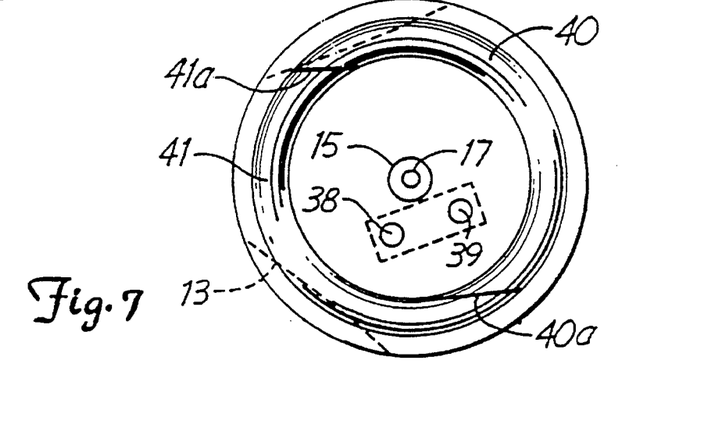
FIG. 7 is a distal end view of the second embodiment.

Referring to FIGS. 5–7, the second embodiment of the probe of this invention, generally designated 37, is substantially the same as the first embodiment other than it contains a single package of two light emitting diodes (light transmitters having distal light transmitting terminal surfaces) 38, 39 that function the same as diodes 25, 27 respectively, but are located on the same radial side of the straight hollow needle 15, and additionally includes a second EKG needle 40 in addition to the EKG needle 41 that is the same as needle 22. Thus the EKG needles form a double spiral and have their sharpened ends 40a, 41a respectively substantially diametrically opposite one another on transverse opposite sides of the needle 15. As illustrated the needles 40, 41 are of shorter spiral lengths than the needle 22. The lead 44 electrically connects the proximal end portions of the spiral needles to one another and extends outwardly of the probe body for direct or indirect (through adaptor 34) connection to the EKG monitor. Further leads 28, 29 connect the diodes directly to the pulse oximeter 19, or indirectly to the oximeter 19 in the same manner indicated for the first embodiment.

It is noted that the first embodiment of the probe may be modified by having the diodes 25, 27 located in a single package on one transverse side of the straight needle such as the situation with the second embodiment and/or provided with a second spiral needle.

Figure 8:
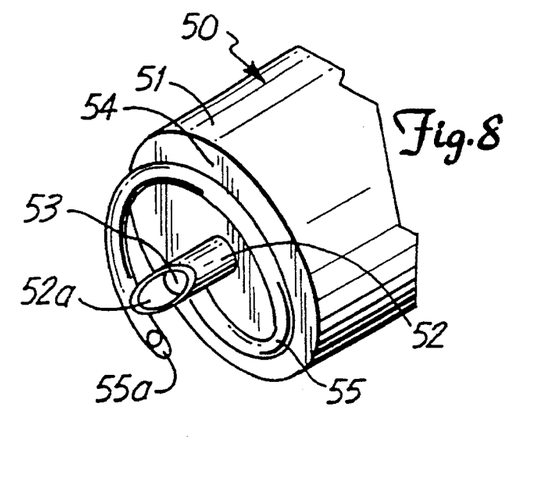
FIG. 8 is a fragmentary perspective distal end view of the third embodiment.
Figure 9:
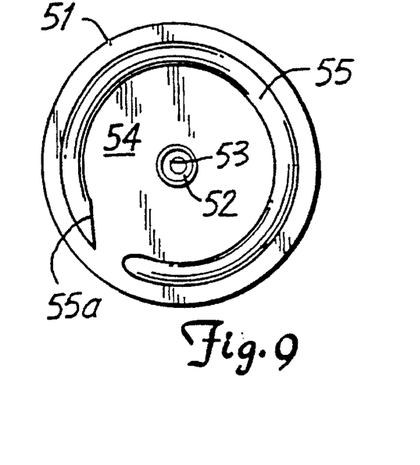
FIG. 9 is a distal end view of the third embodiment.
Figure 10:
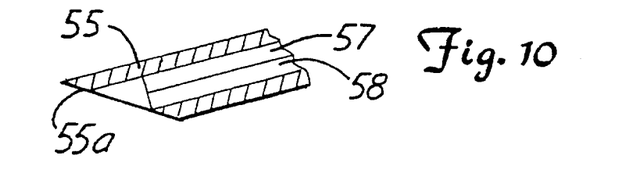
FIG. 10 is a fragmentary view of the distal end portion of the spiral needle of the third embodiment.

Referring now to FIGS. 8–10, the third embodiment of the probe of this invention, generally designated 50, includes a probe body 51, a straight needle 52 and an optical fiber 53 that are substantially the same as the corresponding members 11, 15, 17 of the first embodiment and function in the same manner. Further the probe 50 includes an EKG needle 55 that includes a spiral portion extending distally of the distal transverse surface 54 of the probe body. However, the needle 55 is hollow to have the light transmitting optical fibers 57, 58 extend therethrough to terminate just short of the distal most part of the sharpened edge 55a of the needle. The fiber 57 transmits the visible wavelength light while the fiber 58 transmits the infrared light to the distal terminal end of the needle 55.

The manner of use of the third embodiment is substantially the same as that of the first embodiment other than that the two wave lengths are transmitted from the monitor or adaptor through the respective optical fiber pair 57, 58. It is to be noted that the optical fibers 57, 58 may be in part located in the needle 52 instead of the needle 55, and if so, the optical fiber 53 in part would be located in the needle 55. Advantageously a single fiber may be used in place of fibers 57, 58 to perform the same functions.

Figure 11:
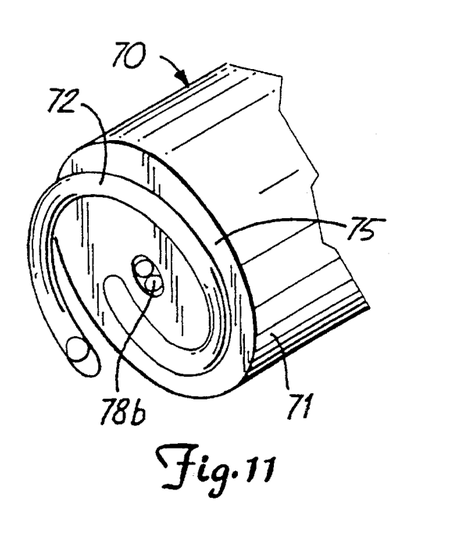
FIG. 11 is a fragmentary perspective distal end view of the fourth embodiment.
Figure 12:
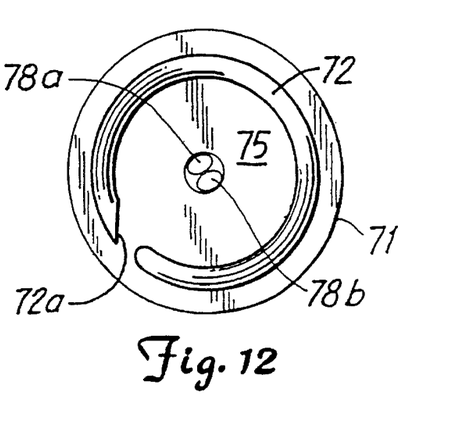
FIG. 12 is a distal end view of the fourth embodiment.
Figures 13, 14, 15, 17:
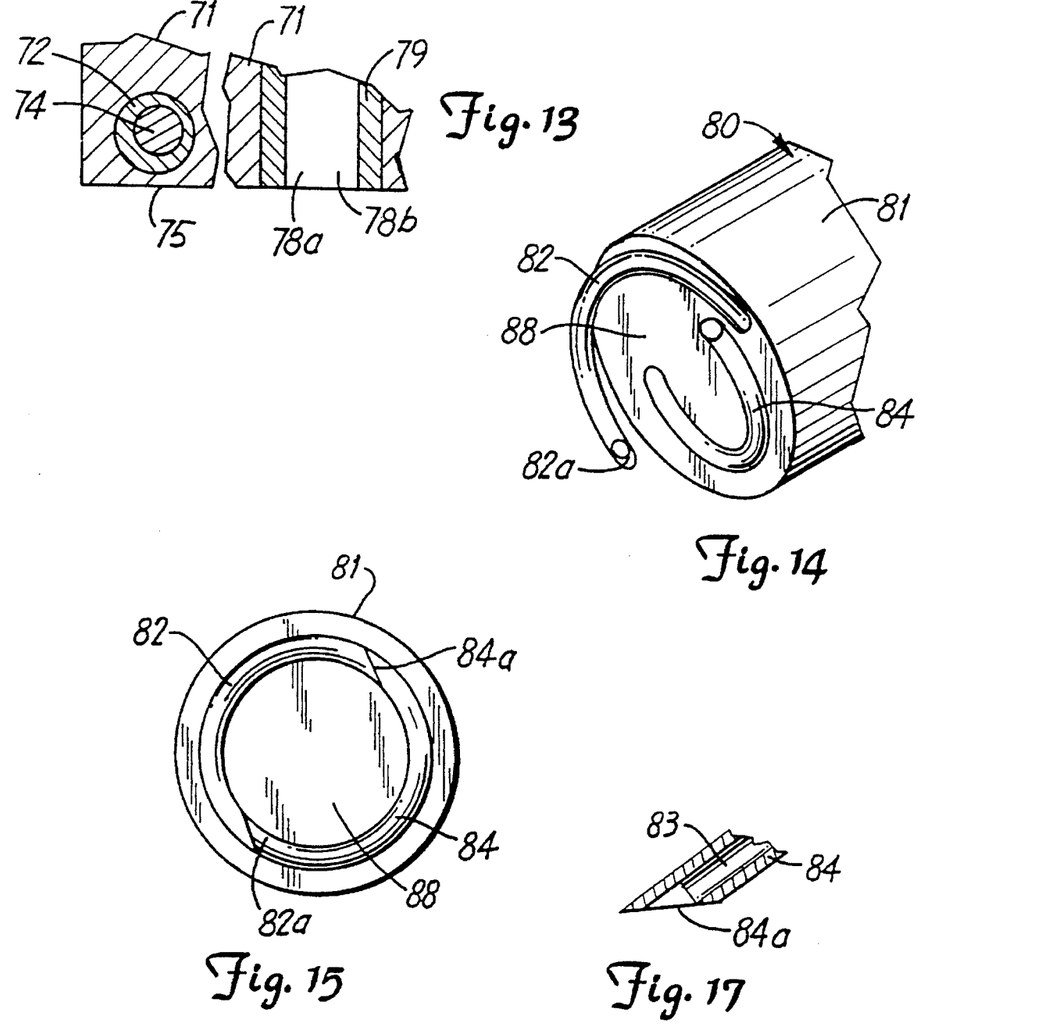
FIG. 13 is a fragmentary cross sectional view of the distal end portion of the probe body of the fourth embodiment to show the optical fibers, one being flush with the distal surface of the probe body and the other being extending within the spiral needle.
FIG. 14 is a fragmentary perspective distal end view of the fifth embodiment.
FIG. 15 is a distal end view of the fifth embodiment.
FIG. 17 is a fragmentary cross sectional view of the distal end portion of the other of the spiral needles.
Figure 16:
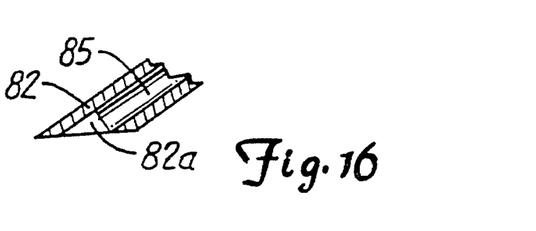
FIG. 16 is a fragmentary cross sectional view of the distal end portion of one of the spiral needles.

Referring to FIGS. 11–13, the fourth embodiment of the probe of this invention, generally designated 70, includes a probe body 71, a hollow EKG needle 72 that at least external of the body is spiral, and an optical fiber (light collector) 74 that extends distally adjacent to the distal sharpened edge 72a of the needle and is connected to the adaptor as is the EKG needle. Further the probe 70 includes a light transmitting optical fiber pair 78a, 78b having their distal ends substantially flush with the distal transverse surface 75 of the probe body and extending generally coextensive with the central axis of the radially adjacent part of the spiral portion of the EKG needle that is within the probe body. The fiber pair 78a, 78b may be located within a tube 79 that has its distal terminate end flush with the surface 75. The fiber 78a transmits visible wavelength light adjacent to surface 75 while fiber 78b transmits infrared wavelength light. Even though a fiber pair has been used, it is to be understood that a single fiber or fiber bundle that performs the same functions may be substituted for fibers 78a, 78b.

Referring to FIGS. 14–17, the fifth embodiment of the probe of this invention, generally designated 80, includes a probe body 81, a hollow EKG needle 82 and a light collecting optical fiber 85 extending within needle 82 that, other than for the angular spiral dimension of the exterior portion of needle 82, are substantially the same as the corresponding members of the third embodiment and function in the same manner. Further the probe 80 includes a hollow second needle 84 having a spiral portion that extends at least distally of the body distal transverse surface 88. The second needle exterior spiral portion has its central axis coextensive with the central axis of the corresponding portion of the needle 82, and of the same external spiral dimension, but has its sharpened terminal edge 84a diametrically opposite the central axes from that of the corresponding edge 82a of needle 82. A light transmitting optical fiber (light transmitter) 83 extends within the needle 84 and has its distal terminal end adjacent to the sharpened edge 84a while the distal terminal end of the fiber (light collector) 85 terminates adjacent to the sharpened edge 82a. The fiber 83 performs the same functions as fibers 57, 58 of the third embodiment. The needle 84 may or may not be electrically connected to the needle 82.

With reference to each of the third, fourth and fifth embodiments the optical fibers and EKG electrode are connected to the EKG and pulse oximeter monitor in a manner similar to the first embodiment and are used in a manner similar to that described with reference to the first embodiment.

Even though the exterior parts of the spiral portion of the needles having spiral needles of the first, third and fourth embodiments are shown as extending angularly a little less than one complete turn; and those of second and fifth embodiments are shown as extending angularly a little more than 180°, it is to be understood that advantageously the exterior spiral portion may extend through about ¾ to 1½ turns.

In each of the embodiments the light collecting fiber is located beneath the skin surface even though in some of the embodiments the light transmitter distal surface is at the skin surface (exterior of the skin surface). That is, at least the distal terminal surface of the light collector is internal to the fetal scalp while the distal terminal surface of the light transmitter may be internal or external of the fetal scalp. Further the entry point of the light collector distal terminal surface is significantly spaced from the light transmitter distal terminal surface to ensure that the optical path is confined to perfused tissue. This eliminates a major source of error in oximetry measurement and one which continues to be a problem in external oximeter probes (neonatal and others). Also with reference to measuring EKG, a second electrode (not shown) may be mounted by the probe body or attached to the mother in a conventional manner.

Even though not preferred, it is to be understood the embodiments may be modified to have their light transmitting distal end surfaces interchanged with the light collector distal end surface including the respective light transmitter and collector members. Further if only one light transmitting fiber is used instead of two, the single fiber would alternately transmit infrared and red wavelength pulses.

Thus there is disclosed herein pulse oximeter EKG apparatus that includes a fetal probe for insertion through the mother's vagina and cervix.

At least each of the straight needles of the first three embodiments and the needles of the fourth and fifth embodiments have hollow tubular portions within the probe body with at least one optical fiber extending therein.

For those embodiments which do not include light emitting diodes within the distal portion of the probe body, it is to be understood that suitable solid state light source and/or detectors may be located within the adaptor and/or the pulse oximeter with their optical inputs and/or outputs connected by means of optical fiber or fibers to the distal portion of the fetal probe (the respective distal end portion of the needle and/or distal surface of the probe body).

What is claimed is:

1. Fetal probe monitoring apparatus for continuously monitoring a constituent of arterial blood of a fetus during labor and delivery, comprising:

a fetal probe body having a longitudinal central axis and a distal end surface;

first means mounted by the probe body for penetrating fetal skin and at least in part removably attaching the body to the fetus, the first means including a first needle mounted by the probe body to extend distally of the body distal surface, the first needle having a distal linear portion extending distally of the probe body surface and having a central axis at least substantially coextensive with the probe body central axis and the first needle having a distal terminal end portion that has an opening to open to fetal tissue inwardly of fetal skin and into perfused fetal tissue;

second means having a distal light collecting surface for collecting light after the light has passed through adjacent perfused fetal tissue;

third means having a distal light transmitting surface for transmitting light to pass through the perfused fetal tissue and then to the second means collecting surface wherein the third means comprise first and second diodes that emit visible and infrared light, respectively, the diodes having the light transmitting surfaces exterior of the fetal skin when the probe body is attached to the fetus and adjacent to the probe body distal surface to transmit light through the fetal skin, the diodes being generally located on diametric opposite sides of the first needle linear portion and transversely spaced from the first needle linear portion;

wherein the second means extends within the first needle to have its distal light collecting surface adjacent to the first needle opening so that the collected light passes through the first needle opening and the third means having its distal light transmitting surface exterior of the first needle and spaced from the first needle sufficiently that light in being transmitted has to travel through perfused tissue prior to being collected, each of the second and third means at least in part extending within the probe body and adjacent to the body distal surface: and a pulse oximeter having means for cooperating with the third means and having means for receiving collected light from the second means for determining the oxygen saturation of arterial hemoglobin.

2. Fetal probe monitoring apparatus for continuously monitoring a constituent of arterial blood of a fetus during labor and delivery, comprising:

a fetal probe body having a longitudinal central axis and a distal end surface;

first means mounted by the probe body for penetrating fetal skin and at least in part removably attaching the body to the fetus, the first means including a first needle mounted by the probe body to extend distally of the body distal surface, the first needle having a distal linear portion extending distally of the probe body surface and having a central axis at least substantially coextensive with the probe body central axis and the first needle having a distal terminal end portion that has an opening to open to fetal tissue inwardly of fetal skin and into perfused fetal tissue;

second means having a distal light collecting surface for collecting light after the light has passed through adjacent perfused fetal tissue;

third means having a distal light transmitting surface for transmitting light to pass through the perfused fetal tissue and then to the second means collecting surface wherein the third means comprise first and second diodes that emit visible and infrared light, respectively, the diodes having the light transmitting surfaces exterior of the fetal skin when the probe body is attached to the fetus and adjacent to the probe body distal surface to transmit light through the fetal skin, the diodes being generally located on the same side of the first needle linear portion and transversely spaced from the first needle linear portion;

wherein the second means extends within the first needle to have its distal light collecting surface adjacent to the first needle opening so that the collected light passes through the first needle opening and the third means having its distal light transmitting surface exterior of the first needle and spaced from the first needle sufficiently that light in being transmitted has to travel through perfused tissue prior to being collected, each of the second and third means at least in part extending within the probe body and adjacent to the body distal surface; and a pulse oximeter having means for cooperating with the third means and having light receiving means for receiving collected light from the second means for determining the oxygen saturation of arterial hemoglobin.

3. Fetal probe monitoring apparatus for continuously monitoring a constituent of arterial blood of a fetus during labor and delivery, comprising:

a fetal probe body having a longitudinal central axis and a distal end surface;

first means mounted by the probe body for penetrating fetal skin and at least in part removably attaching the body to the fetus, the first means including a first needle mounted by the probe body to extend distally of the probe body distal surface, the first needle being generally linear external of the probe body and having a distal terminal end portion that has an opening to open to fetal tissue inwardly of fetal skin and into perfused fetal tissue, the first means further including a spiral second needle extending distally of the probe body distal surface for monitoring EKG;

second means having a distal light collecting surface for collecting light after the light has passed through adjacent perfused fetal tissue; and third means having a distal light transmitting surface for transmitting light to pass through the perfused fetal tissue and then to the second means collecting surface, the distal light transmitting surface being adjacent to the body distal surface and external of both the first needle and the fetal skin;

wherein the second means extends within the first needle to have its distal light collecting surface adjacent to the first needle opening so that the collected light passes through the first needle opening distally remote from the probe body distal surface and the third means has its distal light transmitting surface exterior of the first needle and spaced from the first needle sufficiently that light in being transmitted has to travel through perfused tissue prior to being collected, each of the second and third means at least in part extending within the probe body and adjacent to the body distal surface.

* * * * *

UNITED STATES PATENT AND TRADEMARK OFFICE
CERTIFICATE OF CORRECTION

PATENT NO. : 5,551,424

DATED : SEPTEMBER 3, 1996

INVENTOR(S) : JAMES P. MORRISON, SAMUEL K. YUE

It is certified that error appears in the above-indentified patent and that said Letters Patent is hereby corrected as shown below:

Under Abstract, Line 2, delete "cervixes", insert --cervix--

```
Col. 2, line 47, after "Tension," delete "Inthe", insert--In the--.
Col. 8, line 51, after "surface", delete ":", insert --;--.
```

Signed and Sealed this

Twenty-eighth Day of January, 1997

Attest:

BRUCE LEHMAN

Attesting Officer    Commissioner of Patents and Trademarks